United States Patent [19]

Hall et al.

[11] Patent Number: 5,567,815
[45] Date of Patent: Oct. 22, 1996

[54] TERITARY AMINE CONTAINING ANTONIC INITIATORS USED IN PREPARING POLYMERS AND PROCESS FOR THE PREPARATION THEREOF

[75] Inventors: James E. Hall, Mogadore; David F. Lawson, Uniontown; Thomas A. Antkowiak, Wadsworth, all of Ohio

[73] Assignee: Bridgestone Corporation, Tokyo, Japan

[21] Appl. No.: 276,363

[22] Filed: Jul. 18, 1994

[51] Int. Cl.$^6$ .............. C07D 223/04; C07D 295/04
[52] U.S. Cl. .............. 540/541; 540/465; 544/64; 544/4; 544/225; 546/11; 548/101; 556/1; 502/157
[58] Field of Search .............. 540/541, 465; 544/4, 64, 225; 546/11; 548/101, 402; 556/1; 502/157

[56] References Cited

U.S. PATENT DOCUMENTS 5,039,814  8/1991  Shuman et al. ............. 548/250
5,153,159  10/1992  Antkowiak et al. ............. 502/155

OTHER PUBLICATIONS

Katritzky, A. R. *Handbook of Heterocyclic Chemistry* (Pergemon Press, Oxford), pp. 148 and 151 (1985).

*Primary Examiner*—Mukund J. Shah
*Assistant Examiner*—King Lit Wong
*Attorney, Agent, or Firm*—Frank J. Troy, Sr.

[57] ABSTRACT

An anionic initiator system formed by the reaction product of: (1) an organolithium compound with (2) the reaction product of (a) a secondary amine and (b) diisopropenyl benzene, initiates polymerization to produce a polymer containing tertiary amine functional sites incorporated at the head of the polymer chain. A subclass of these polymers can be compounded to exhibit reduced hysteresis over conventionally prepared polymers.

7 Claims, No Drawings

5,567,815

TERITARY AMINE CONTAINING ANTONIC INITIATORS USED IN PREPARING POLYMERS AND PROCESS FOR THE PREPARATION THEREOF

FIELD OF THE INVENTION

This invention relates to an anionic polymerization of diene monomers and comonomers to produce polymer and copolymer elastomers having a tertiary amine group on the initiated end of each polymer chain. More specifically, the present invention relates to an anionic initiator system formed by sequentially reacting diisopropenyl benzene with a secondary amine and then with an organolithium compound to prepare diene polymers and copolymers having reduced hysteresis characteristics.

Articles such as tires, power belts and the like prepared from these polymers or copolymers exhibit increased rebound, decreased rolling resistance and less heat build-up during mechanical stress operation.

BACKGROUND OF THE INVENTION

It is desirable to produce elastomeric compounds exhibiting reduced hysteresis. Such elastomers, when compounded to form articles such as tires, power belts and the like, show an increase in rebound and a decreased rolling resistance and display less heat build-up when mechanical stresses are applied.

Previous attempts at preparing reduced hysteresis products have included high temperature mixing of the filler-rubber mixtures in the presence of selectively reactive promoters to promote compounding material reinforcement; surface oxidation of the compounding materials; chemical modifications to the terminal end of polymers using tetramethyldiaminobenzophenone (Michler's ketone), tin coupling agents and the like and, surface grafting thereon. All of these approaches have focused upon increased interaction between the elastomer and the compounding materials.

It has also been recognized that carbon black, employed as a reinforcing filler in rubber compounds, should be well dispersed throughout the rubber in order to improve various physical properties. One example of the recognition is provided in published European Patent Application EP 0 316 255 A2 which discloses a process for end capping polydienes by reacting a metal terminated polydiene with a capping agent such as a halogenated nitrile, a heterocyclic aromatic nitrogen containing compound or an alkyl benzoate. Additionally, the application discloses that both ends of the polydiene chains can be capped with polar groups by utilizing functionalized initiators, such as lithium amides.

U.S. Pat. No. 5,153,159, to Antkowiak et al, discloses an anionic polymerizing initiator formed by the reaction product of a functionalizing agent selected from the group consisting of substituted aldimines, ketimines and secondary amines, and an organolithium compound. These initiators are used to prepare elastomeric polymers having functional sites at the initiator end of the polymer chain and exhibiting reduced hysteresis, however their use produces undesirable side effects. Since these functionalizing agents initiate polymerization from a nitrogen atom initiation rates are low and termination reactions occur that promote undesirable branching. Furthermore, only batch polymerization techniques can be employed utilizing the nitrogen atom initiated polymerizations since lower reaction temperatures must be maintained to limit side reactions.

OBJECTS OF THE INVENTION

It is therefore an object of the present invention to provide anionic initiators that produce polymer chains having tertiary amine functional end groups at increased initiation rates.

It is another object of the invention to provide a method of preparing an anionic polymerization initiator that is stable under semibatch and continuous polymerization operations.

It is another object of the present invention to provide an anionic initiator for preparing functionalized polymers having active terminal groups in semi-batch and continuous commercial processes.

It is another object of the present invention to provide anionic initiators capable of producing vulcanizable elastomeric compounds having reduced hysteresis at elevated temperatures.

These and other objects together with the advantages thereof over the existing art, which shall become apparent from the specification which follows, are accomplished by the invention as hereinafter described and claimed.

SUMMARY OF THE INVENTION

The present invention relates to anionic initiators used in preparing functionalized polymers by the steps of forming a solution of one or more anionically polymerizable monomers in a solvent and, initiating the polymerization of the monomers. The anionic initiator is formed by the reaction product of: (1) an organolithium compound and (2) a precursor functionalizing agent formed by the reaction of a secondary amine and DIPB, wherein a functional group derived from the reaction product is incorporated onto the polymer chain at the initiator end and the lithium atom from the organolithium compound is carried at the other end of the polymer prior to quenching. The anionic initiator is used to produce functionalized polymers having a polymer chain carrying a functional group X at the initiator end, wherein the functional group X is derived from the reaction product X-Li of an organolithium compound and a precursor functionalizing agent, the precursor functionalizing agent being formed by pre-reacting diisopropenyl benzene (DIPB) and a secondary amine. A heterocyclic ring containing compound having a nitrogen atom of a secondary amine as a ring atom is preferred. The polymer chain of the functionalized polymer has a lithium atom from the organolithium compound carried at the other or living end of the polymer chain prior to quenching.

According to the present invention vulcanizable elastomeric polymers having reduced hysteresis properties can be produced. The elastomeric polymer has chains carrying the functional group X at the initiator end, wherein X-Li is the reaction product of an organolithium compound and a precursor functionalizing agent formed by the reaction of a heterocyclic ring containing a nitrogen atom in the ring from a secondary amine and DIPB; and the lithium atom from the reaction product attaches on the living end of the polymer and is carried at the other end of the polymer chain prior to quenching. The elastomeric polymer is additionally blended with from about 5 to 80 parts by weight of carbon black, per 100 parts of the polymer.

An improved tire tread, sub-tread, body ply, sidewall and other parts of the tire, singly or in combinations, having decreased rolling resistance is produced from rubber stocks containing the vulcanizable elastomeric composition produced according to the present invention and from about 5 to 80 parts by weight of carbon black, per 100 parts of the polymer.

DETAILED DESCRIPTION OF THE INVENTION

AS will become apparent from the description which follows, the present invention provides a novel initiator for anionic polymerization of diene homopolymer and copolymer elastomers, as well as homopolymers of polyethylene and of poly(vinyl aromatic monomers). Polymers prepared with these initiators contain a tertiary amine as a terminal group. The vulcanizable elastomeric compounds and articles prepared from heterocyclic ring containing tertiary amine initiators contain functionally terminated polymers exhibiting useful properties, particularly exhibiting reduced hysteresis. Hysteresis is generally known as the failure of a property that has been changed by an external agent to return to its original value when the cause of the change is removed. When compounded to make products such as tires, power belts and the like, these polymeric products exhibit increased rebound, decreased rolling resistance and less heat build-up during periods of applied mechanical stress.

The initiators, according to the present invention, are anionic and are formed by the reaction of (1) an organolithium compound and (2) a precursor functionalizing agent that is formed by reacting a secondary amine and diisopropenyl benzene (DIPB). The organolithium compound has the general formula RLi where R is selected from the group consisting of alkyls, cycloalkyls, alkenyls, alkynyls, aryls and aralkyls having from 1 to about 20 carbon atoms and short chain length low molecular weight polymers from diolefin and vinyl aryl monomers having up to about 25 units. Typical alkyls include n-butyl, s-butyl, methyl, ethyl, isopropyl and the like. The cycloalkyls include cyclohexyl, cyclopentyl and the like. The alkenyls include allyl, vinyl and the like. The aryl and aralkyl groups include phenyl, benzyl, oligo(styryl) and the like. Exemplary short chain length polymers include the oligo(butadienyls), oligo(isoprenyls), oligo(styryls) and the like.

In the production of the precursor functionalizing agent, the secondary amine can either be a non-cyclic amine or a heterocyclic ring containing secondary amine. The secondary amines useful in the present invention are displayed in Formula (I):

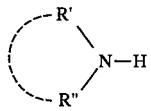
(I)

wherein R' and R" are the same of different and are any substituents that are non-reactive with lithium or DIPB including but not limited to $C_{1-20}$ alkyl groups and $C_{4-20}$ cycloalkyl groups such as methyl, ethyl, propyl, butyl, octyl, cyclohexyl and the like or aryl groups, alkoxy groups, alkyoxyalkyl groups, arylalkyl groups and the like. The R' and R" can also be joined to form a heterocyclic ring containing secondary amine. The heterocyclic ring containing secondary amine can be any heterocyclic compound containing only one secondary amine group in the ring with the proviso that the heterocyclic compound can contain no substituents that are reactive with lithium or DIPB other than the secondary amine. Representative heterocyclic compounds useful in the present invention as represented by formula (I) wherein the ring of formula (I) represents any heterocyclic ring compound containing a nitrogen atom of a secondary amine as a ring atom and the heterocyclic ring is free of substituents or unsubstituted ring atoms, primarily non-carbon atoms, that are reactive with either lithium or alkylene groups. The heterocyclic compounds of formula (I) include but are not limited to: morpholine, thiomorpholine, N-(lower alkyl)-piperazine, N-aryl-piperazine, 1-(2-pyridyl)-piperazine, pyrrole, 3-pyrroline, pyrazole, imidazole, imidazoline, indole, indoline, purine and azacycloalkanes. The ring linkage represented by —R'–R"— in Formula (I) is preferably —$(CH_2)_2$—O—$(CH_2)_2$—; —$(CH_2)_2$—S—$(CH_2)_2$—; —$(CH_2)_2N(R^1)$—$(CH_2)_2$—; or —$(CH_2)_p$— wherein p is an integer from 3 to about 20, preferably 4 to 12, and $R^1$ is a substituent group that is non-reactive with lithium or DIPB, preferably a lower alkyl group. Preferably the —R'–R"— linkage groups are methylene group bonding with the nitrogen atom to form an azacycloalkane heterocyclic ring having a total of 4 to 21 ring atoms, preferably 5 to 13 ring atoms. The heterocyclic ring compounds of formula (I) can be optionally substituted with one or more, preferably one to four substituents that are non-reactive with lithium or DIPB including but not limited to: alkyl groups and cycloalkyl groups such as methyl, ethyl, propyl, butyl, octyl, cyclohexyl and the like or aryl groups, alkoxy groups, alkyoxyalkyl groups, arylalkyl groups and the like. Exemplary azacycloalkanes are $HN(CH_2)_5$, namely, piperidine; $HN(CH_2)_4$, namely, pyrrolidine; $HN(CH_2)_6$, namely, hexamethyleneimine; and $HN(CH_2)_{12}$, namely, dodecamethyleneimine. Other preferred heterocyclic secondary amines include morpholine and N-methyl-piperazine.

These secondary amines are reacted with diisopropenyl benzene (DIPB) represented by the formula (II):

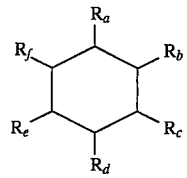
(II)

wherein two of the $R_a$, $R_b$, $R_c$, $R_d$, $R_e$ and $R_f$ radicals are isopropenyl radicals and each of the remaining $R_a$–$R_f$ radicals are independently hydrogen or an alkyl or cycloalkyl radical containing 1 to 6 carbon atoms.

The reaction product of DIPB with a secondary amine results in the formation of a precursor functionalizing agent containing a tertiary amine having the structure (III):

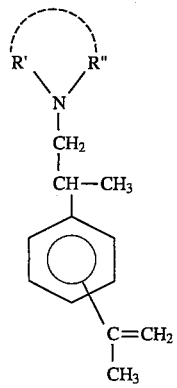
(III)

Preferably the DIPB is reacted with the secondary amine in, at least, a 1:1 ratio, so that a second pendent isopropenyl group on the DIPB remains unreacted for subsequent reaction with the organolithium compound. The formation of the precursor functionalizing agent is preferably conducted in an aprotic solvent such as hexane if it is to be used without further purification. Alternatively the precursor functionalizing agent must be purified before further use.

The precursor functionalizing agent is formed by: (1) reacting a secondary amine (Formula I) and diisopropenyl benzene (Formula II), and (2) subsequently reacting the precursor functionalizing agent (formula III) formed in step (1) with RLi to form a funtionalizing agent, X-Li, as displayed in formula (IV):

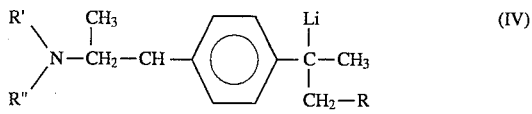

and wherein R, R' and R" have been previously defined and the secondary amino radical is the radical remaining upon the removal of the secondary amino hydrogen (R'—N H—R") from the secondary amine compound of formula (I).

The initiators or functionalizing agents of the present invention are used to polymerize monomers into "living polymers" The general formula of a "living polymer" containing a functionalizing group X of the functionalizing agent X-Li is displayed in formula (V):

X–polymer–Li                                    (V)

wherein the polymer is any of the foregoing diene homopolymers, monovinyl aromatic homopolymers, diene/ monovinyl aromatic random copolymers and block copolymers and X is the radical or functionalizing group remaining from the functionalizing agent after the lithium atom has initiated polymerization of monomers and has been separated from the functionalizing agent and removed and transported along the polymer chain. The lithium moves down the growing chain as polymerization continues. It should be apparent that the lithium atom from the reaction product X is carried by the other end of the growing polymer chain as depicted hereinabove, until the reaction is quenched.

The initiator, also called the functionalizing agent, is anionic and according to the present invention can be produced by preparing a solution of the precursor functionalizing agent in an anhydrous, aprotic solvent, such as hexane. To this solution is then added the organolithium catalyst (RLi) in the same or a similar solvent. The precursor functionalizing agent and the RLi are allowed to react for an appropriate period of time, e.g. 24 hours at 25° C., or 20 minutes at 50° C., after which time the catalyst is ready for use. It is not necessary to remove the solvent inasmuch as the anionic polymerization is conducted in the same or a compatible solvent. Amounts of the two reactants range from about 0.2 to 3.0 mmoles of precursor functionalizing agent to 1.0 mmole of organolithium catalyst, with equimolar parts being preferred. It is to be appreciated by one skilled in the art that various reaction temperatures and times may be useful and are within the scope of the present invention.

The amount of initiator or functionalizing agent to be used in the polymerization process depends upon the type of polymer desired. An effective initiator level is normally in the range of about 0.25 to 100, preferably 0.50 to 2.0 milliequivalents of effective lithium per 100 grams of monomer charged to the polymerization system. Effective lithium is the amount of lithium able to initiate and propagate polymer chains after impurities such as water have been reacted.

As stated above, the initiator acts as a functionalizing agent and is employed to initiate and prepare any anionically polymerized polymer, e.g. polybutadiene, polyisoprene and the like, and copolymers thereof with monovinyl aromatics such as styrene, alpha-methylstyrene and the like, or trienes such as myrcene, and other polymers that are known to be polymerizable by anionic organolithium initiators, e.g. polyethylene, poly(vinyl aromatic hydrocarbons) such as polystyrene, and the like. Thus, the elastomers include diene homopolymers and copolymers thereof with monovinyl aromatic polymers. Exemplary diene homopolymers are those prepared from diolefin monomers having from 4 to about 12 carbon atoms. Exemplary vinyl aromatic hydrocarbon polymers, such as polystyrene, are those prepared from monomers having from 8 to about 20 carbon atoms. Preferred polymers produced in accordance with the process of the present invention are polyethylene and polystyrene and elastomers including diene homopolymers such as polybutadiene and polyisoprene and copolymers such as styrene butadiene rubber (SBR). Polymers and copolymers can contain from about 100 to 30 percent by weight of diene units and from about 0 to 70 percent by weight of monovinyl aromatic hydrocarbon or triene units, totalling 100 percent. The polymers and copolymers of the present invention may have 1,2-microstructure contents ranging from about 8 to about 100 percent, with the preferred polymers or copolymers having 1,2-microstructure contents of from about 10 to 70 percent, based upon the diene content.

The copolymers are preferably random copolymers resulting from simultaneous copolymerization of the monomers forming polymers with random distribution of A and B monomers, as is known in the art. The block copolymers, e.g. poly (b-B-b-A-b-B), result from the separate polymerization of the monomers forming the B-A-B polymers as is known in the art. Such block copolymers which include poly(styrene-butadiene-styrene) are thermoplastic elastomers.

Polymerization is usually conducted in a conventional solvent for anionic polymerizations such as hexane, cyclohexane, benzene, tetrahydrofuran and the like. Techniques for polymerization such as batch, semi-batch and continuous polymerization may be employed. The novel initiators of the present invention are particularly useful for semi-batch and continuous polymerizations of butadiene, isoprene, and styrene as prior techniques using lithium amides or initiators having initiation beginning from a nitrogen atom have generally resulted in polymerizations that have self-terminated before all the monomers have polymerized.

In order to promote randomization in copolymerization and to increase vinyl content, a modifier may optionally be added to the polymerization ingredients. Amounts range between 0 to 90 or more equivalents per equivalent of lithium. The amount depends upon the type of modifier and the amount of vinyl desired, the level of styrene employed and the temperature of the polymerizations, as well as the precursor functionalizing agent selected to form the initiator.

Compounds useful as modifiers are organic and include those having an oxygen or nitrogen hetero-atom and a non-bonded pair of electrons. Examples include dialkyl ethers of mono and oligo alkylene glycols; "crown" ethers; tertiary amines such as tetramethylethylene diamine (TMEDA); tetrahydrofuran (THF), THF oligomers such as linear and cyclic oligomeric oxolanyl alkanes as described in U.S. Pat. No. 4,429,091, the subject matter of which is herein incorporated by reference.

Polymerization is begun by charging one or more monomers and solvent to a suitable reaction vessel, followed by the addition of the modifier and the initiator solution previously described. The procedure is carried out under anhydrous, anaerobic conditions. The reactants are heated to a temperature of from about −30° to 150° C. and are agitated for about 0.15 to 24 hours. After polymerization is complete, the polymer product is terminated in one or more ways. For example, a protic quenching agent may be employed to give a monofunctional polymer chain. Quenching may be conducted in water, steam or an alcohol such as isopropanol, or any other suitable method.

Alternatively, the polymer may be terminated with another reactive molecule to form a difunctional polymer. Examples would include tin tetrachloride; Michler's ketone; 1,3-dimethyl-2-imidazolidinone; 1-alkyl substituted pyrrolidones, e.g., methyl, 1-methyl-2-pyrrolidone, ethyl, propyl, butyl and the like; 1-aryl substituted pyrrolidones, e.g., phenyl, and the like; certain Schiff bases and the like.

Further examples of reactive molecules include the terminators described in U.S. Pat. No. 5,066,729, the subject matter of which is incorporated by reference herein. It is to be understood that practice of the present invention is not limited solely to test terminators inasmuch as other compounds that are reactive with the polymer bound carbon-lithium moiety can be selected to provide a desired functional group. Furthermore, coupling agents may be used as displayed in the following examples including $SnCl_4$, dimethyl silicon dichloride, dihaloalkanes such as dibromoethane and dibromoxylene, esters such as methyl benzoate, phosphonitrilic chloride trimer and tetramer and the like to produce polymers that have functional groups X on both ends of the polymer chain.

Quenching is usually conducted by mixing the polymer and quenching agent for about 0.05 to about 2 hours at temperatures of from about 30° to 120° C. to insure complete reaction. Polymers terminated with a functional agent such as a Schiff base and the like, are subsequently quenched with alcohol or other quenching agent as described hereinabove.

Lastly, the solvent is removed from the polymer by drum drying, extruder drying, vacuum drying or the like, which may be combined with coagulation with water, alcohol or steam. If coagulation with water or steam is used, oven drying may be desirable.

The polymers of the present invention contain a functional group at the head or, if coupled, at both ends of the polymer chain rather than only at the terminal end of the chain. These functional groups can have an affinity for compounding materials such as carbon black. Such compounding results in products exhibiting reduced hysteresis, which means a product having increased rebound, decreased rolling resistance and exhibiting reduced heat build-up when subjected to mechanical stress. The elastomers of the present invention are useful for producing products including tires, power belts and the like. Decreased rolling resistance is, of course, a useful property for pneumatic tires, both radial as well as bias ply types and thus, the vulcanizable elastomeric compositions of the present invention can be utilized to form treadstocks, sidewalls, body plies and other parts for such tires.

The polymers of the present invention can be utilized as 100 parts of the rubber in the treadstock compound or, they can be blended with any conventionally employed treadstock rubber which includes natural rubber, synthetic rubber and blends thereof. When the polymers of the present invention are blended with conventional rubbers, the amounts can vary widely with a lower limit comprising about 10 to 20 percent by weight of the total rubber. It is to be appreciated that the minimum amount will depend primarily upon the degree of reduced hysteresis that is desired.

The polymers can be compounded with all forms of carbon black in amounts ranging from about 5 to 80 parts by weight, per 100 parts of rubber (phr), with about 35 to 60 phr being preferred. The reinforced rubber compounds can be cured in a conventional manner with known vulcanizing agents at about 0.1 to 10 phr. For a general disclosure of suitable vulcanizing agents one can refer to Kirk-Othmer, Encyclopedia of Chemical Technology, 3rd ed., Wiley Interscience, N.Y. 1982, Vol. 20, pp. 365–468, particularly "Vulcanization Agents and Auxiliary Materials" pp. 390–402. Vulcanizing agents can be used alone or in combination.

Vulcanizable elastomeric compositions of the invention can be prepared by compounding or mixing the functionalized polymers herein with carbon black and other conventional rubber additives such as fillers, plasticizers, antioxidants, curing agents and the like using standard rubber mixing equipment and procedures. Such elastomeric compositions when vulcanized using conventional rubber vulcanization conditions can have reduced hysteresis properties and are particularly adapted for use as tread rubbers for tires having reduced rolling resistance.

In order to demonstrate the preparation and properties of elastomers prepared according to the present invention, in Examples 1 to 18 a functional initiator was prepared by treating a precursor functionalizing agent, formed by reacting equal molar amounts of diisopropenyl benzene and hexamethyleneimine to produce 2-(1-hexamethyleneimino)-propyl-3-isopropenyl benzene (HMIPB) with s-butyl lithium under an inert atmosphere. The initiator was then used to prepare a elastomer in solution and under an inert atmosphere. The termination reactions involved quenching with isopropanol or coupling with $SnCl_4$. As noted above, various techniques known in the art for carrying out polymerizations may be used with these initiators without departing from the scope of the present invention.

EXAMPLE 1

A bake-dried, nitrogen purged one gallon stainless steel reactor was treated with a rinse of hexane containing 10 mmoles of n-butyl lithium and charged with 500 g of 1,3-butadiene and 2000 g of hexane. The functional initiator was prepared by reacting equal amounts of 2-(1-hexamethyleneimino)propyl-3-isopropenyl benzene (HMIPB) and s-butyl lithium at a one molar concentration in hexane for two hours at 25° C. and then diluting to 0.02 molar in hexane and heating at 65° C. for 15 minutes. A charge of 4.5 mmoles of this functional initiator was added to the one gallon reactor and polymerization proceeded to completion at 50° C. for 4 hours. After polymerization was completed the reaction was quenched with isopropanol and the polymer was recovered by drum-drying. The recovered polybutadiene had a molecular weight of 140,700, a $M_w/M_n$ of 1.31 and a microstructure containing 36.5% cis-1,4-units, 52.7% trans 1,4-units and 10.8% vinyl units.

EXAMPLE 2

A one gallon reactor was prepared as in Example 1 and was charged with 100 g of styrene, 400 g. of 1,3-butadiene and 2000 g of hexane. HMIPB was reacted with an equivalent amount of s-butyl lithium at a 0.02 molar concentration in hexane for 15 minutes at 65° C. to form the functional initiator. The reactor was then charged with 4.5 mmoles of the functional initiator and 2.25 mmoles of 2,2-di (tetrahydrofuryl) propane as a randomizer and to increase the vinyl content of the butadiene monomer contributed units. The polymerization was conducted at 55° C. for two hours. The reaction was quenched with isopropanol and the SBR copolymer was recovered by drum-drying. The SBR copolymer had a molecular weight of 155,100, a $M_w/M_n$ of 1.31, a vinyl content of 68.2% in the butadiene monomer contributed units and contained 21.9% by weight of styrene.

EXAMPLE 3 (Comparative)

A control SBR copolymer was prepared in accordance with the procedure of Example 2, however the initiator consisted solely of 4.5 mmoles of n-butyl lithium. The recovered SBR copolymer had a molecular weight of 134,800, a $M_w/M_n$ of 1.32, a 69.3% vinyl content in the butadiene monomer contributed units, and contained 22.2% by weight of styrene.

EXAMPLES 4 TO 10

These examples display the preparation of SBR in a semibatch process. As identified in Table 1, a functional initiator was prepared by reacting displayed amounts of HMIPB with either s- or n-butyl lithium at 95° C. for 10 to 15 minutes in hexane at a 0.10 molar solution. Additionally, each catalyst system employed 0.25 mmoles of 2,2-di(tetrahydrofuryl) propane as a randomizer and to increase the vinyl content of the butadiene contributed units, except Example 6 employed only 0.2 mmoles of randomizer.

In each of Examples 4 to 10, a steel reactor was charged with the amounts of functionalized initiator as prepared in 0.1 molar concentrations in hexane in the reactive amounts identified in Table 1 and with the modifier.

A blend of 65% 1,3-butadiene/35% styrene in hexane was metered into the reactor for 90 to 105 minutes at 90° to 100° C. and polymerized. Polymerization was terminated with isopropanol (i-PrOH) or a $SnCl_4$ coupling agent and the copolymers were recovered by drum drying. The properties of the recovered styrene-butadiene copolymers are displayed in Table 1. Polymer analyses were conducted by GPC to provide molecular weight values and by NMR to provide amounts of 1,2-content of the diene units expressed as a percent, as well as the percent of bound styrene and block styrene. Block styrene as determined by $^1H$ NMR is the percent of styrene present in blocks of greater than three styrene monomer units. Additionally the recovered copolymers, Examples 6 and 10 displayed coupling of 40% and 66%, respectively. Example 4 was a control characterizing conventional anionic polymerization.

EXAMPLES 12 AND 13

The recovered polybutadiene polymer from Example 1 was compounded with 50 pbw of carbon black and 10 pbw of naphthenic oil plus standard sulfur curatives and the vulcanized compound displayed a tan δ at 50° C. of 0.093 as Example 12.

A polymer was produced in accordance with the procedure of Example 1, however the functional initiator was replaced with s-butyl lithium. The recovered control polybutadiene polymer was compounded with 50 pbw of carbon black and 10 pbw of naphthenic oil and standard sulfur curatives as in Example 13. The original polybutadiene possessed the following properties: 10% vinyl content, $M_n$ of 94,200, $M_w/M_n$ of 1.23; and the recovered vulcanizate displayed a tan δ at 50° C. of 0.186.

EXAMPLES 14 AND 15

The styrene-butadiene copolymers prepared in Examples 2 and 3 were each compounded with 50 pbw of carbon black and 10 pbw of naphthenic oil and sulfur cured. The compounded styrene-butadiene copolymer of Example 2 displayed a tan δ at 50° C. of 0.128 as Example 14. The compounded styrene-butadiene copolymer of Example 3 displayed a tan δ at 50° C. of 0.230 as Example 15.

EXAMPLES 16 TO 18

Recovered semibatch styrene-butadiene copolymers were compounded with 15 pbw of naphthenic oil per hundred parts by weight of copolymer and 48.5 pbw of carbon black. The copolymer employed in Example 16 was the recovered SBR copolymer of Example 4. The copolymer employed in Example 17 was the recovered SBR copolymer of Example 7. The copolymer employed in Example 18 was the recovered SBR copolymer of Example 6. The tan δ at 50° C. for Example 16, containing the copolymer of Example 4, the control, was 0.179 and the compound $ML_4$ at 100° C. was 61. The tan δ at 50° C. and compound $ML_4$ at 100° C. for Examples 17 was 0.127 and 60, respectively, and for

TABLE I

| Example No. | 4 | 5 | 6 | 7 | 8 | 9 | 10 |
|---|---|---|---|---|---|---|---|
| Anionic Initiator | n-BuLi | n-BuLi | n-BuLi | s-BuLi | s-BuLi | s-BuLi | s-BuLi |
| mmoles (BuLi) | 5 | 5.5 | 5.5 | 6 | 5 | 3.7 | 4 |
| HMIPS (mmoles) | 0 | 5.5 | 5.5 | 4.5 | 4.5 | 3.7 | 4 |
| Terminator | i-PrOH[a] | i-PrOH | $SnCl_4$ | i-PrOH | i-PrOH | i-PrOH | $SnCl_4$ |
| Yield (%) | 95 | 94 | 95 | 90 | 92 | 91 | 96 |
| $ML_4$, 100° C. | 40 | 47 | 162 | 29 | Low | 64 | 110 |
| % 1,2 | 17.7 | 18.9 | 18.5 | 17.8 | 15.1 | 18 | 18.6 |
| % Bound Styrene | 36.1 | 36.8 | 37.7 | 36.4 | 34.4 | 35.4 | 36.4 |
| % Block Styrene | 8.4 | 12.5 | 16.8 | 10.6 | 9.2 | 14.1 | 17.4 |
| Mn/1000 | 134.7 | 126.9 | 199.5 | 110.6 | 88.7 | 147.1 | 214.5 |
| Mw/1000 | 167.8 | 170.6 | 434.6 | 141 | 112 | 209 | 547.3 |
| Mw/Mn | 1.25 | 1.34 | 2.18 | 1.27 | 1.26 | 1.42 | 2.55 |

EXAMPLE 11 (Comparative)

A semibatch polymerization was run in accordance with the procedures of Examples 4 to 10, employing an anionic initiator system of a 50/50 mixture of lithium pyrrolidinide and lithium hexamethyleneimide. The polymerization died out achieving only 65% conversion of monomer.

Example 18 was 0.108 and 87, respectively.

Inasmuch as a lower tan δ value indicates improved hysteresis, it is readily noted that Examples 17 and 18, containing the copolymers of Examples 7 and 6, respectively, prepared with an initiator of the present invention showed a most favorable improvement in hysteresis over the control polymer of Example 16.

In conclusion, it should be clear from the foregoing examples and specification disclosure that the initiators of the present invention are useful for the anionic polymerization of diene monomers to form homopolymers as well as copolymers with monovinyl aromatic polymers or trienes. The resulting elastomeric polymers have a functional group at the site of initiation and a lithium atom at the terminal, "living" end. After quenching, the polymers still retain the functional group at the site of initiation, which promotes uniform and homogeneous mixing with carbon black. As a result vulcanizable elastomeric compounds containing these polymers exhibit improved hysteresis which provides lower rolling resistance in tires and improved fuel economy. Additionally, the lithium terminated polymers can be quenched with compounds to provide terminal functional groups and hence, difunctional polymer chains.

EXAMPLES 19 TO 23

In the following examples, styrene butadiene rubber compositions were prepared utilizing in situ dispersion polymerization techniques disclosed in Examples 3 to 12 in copending patent application U.S. Ser. 995,118, filed on Dec. 22, 1992 to James Hall, which is herein incorporated by reference.

Example 19 is a comparative example and utilized a n-butyllithium initiator. Example 20 utilized an initiator (PYRPB) formed by a 1:1 molar ratio of (a) n-butyllithium and (b) equal molar amounts of pyrrolidine and diisopropenylbenzene. Example 21 utilized an initiator (PIPPB) formed by a 1:1 molar ratio of (a) n-butyllithium and (b) equimolar amounts of piperidine and diisopropenylbenzene. Example 22 utilized an initiator (HMIPB) formed by a 1:1 molar ratio of (a) n-butyllithium and (b) equimolar amounts of hexamethyleneimine and diisopropenylbenzene. Example 23 utilized an initiator formed by a 1:1 molar ratio of (a) n-butyllithium and (b) the reaction product of equimolar amounts of diethylamine and diisopropenylbenzene. Table 2 displays the properties of the recovered styrene-butadiene rubber (SBR) polymers as well as the vulcanizate properties of these SBR polymers after compounding with 48.5 parts by weight of carbon black and 15 parts by weight of naphthenic oil per 100 parts of rubber and curing with sulfur.

It is to be understood that the invention is not limited to the specific precursor functionalizing agents and organolithium compounds disclosed nor to any particular modifier or solvent. Similarly, the examples have been provided merely to demonstrate practice of the subject invention and do not constitute limitations of the invention. Those skilled in the art may readily select other monomers and process conditions, according to the disclosure made hereinabove.

Thus, it is believed that any of the variables disclosed herein can readily be determined and controlled without departing from the scope of the invention herein disclosed and described. Moreover, the scope of the invention shall include all modifications and variations that fall within the scope of the attached claims.

TABLE II

| EXAMPLE NO. | 19 | 20 | 21 | 22 | 23 |
|---|---|---|---|---|---|
| INITIATOR | n-BuLi | n-BuLi + PYRPB | n-BuLi + PIPPB | n-BuLi + HMIPB | n-BuLi + ET$_2$NPB |
| TERMINATOR | Me$_2$SiCl$_2$ | Me$_2$SiCl$_2$ | Me$_2$SiCl$_2$ | Me$_2$SiCl$_2$ | Me$_2$SiCl$_2$ |
| % COUPLED | 37 | 65 | 72 | 67 | 54 |
| GPC | | | | | |
| $M_n$ | 112,500 | 103,200 | 121,300 | 110,000 | 95,600 |
| $M_w/M_n$ | 1.92 | 1.9 | 1.82 | 1.73 | 1.76 |
| H NMR | | | | | |
| % 1,2-vinyl | 21.4 | 21.2 | 20.4 | 20.5 | 19.7 |
| % STYRENE | 44 | 43.2 | 44.7 | 41.8 | 41.3 |
| % BLOCK STYRENE | 8.5 | 11.9 | 16.7 | 9.1 | 8.2 |
| ML-4 @ 100° C. | 45 | 58 | 63 | 34 | 38 |
| | | | VULCANIZATE PROPERTIES | | |
| ML-4 @ 100° C. | 53 | 73 | 66 | 64 | 50 |
| TAN DELTA @ 23° C. | 0.283 | 0.188 | 0.215 | 0.166 | 0.253 |
| TAN DELTA @ 50° C. | 0.203 | 0.166 | 0.135 | 0.106 | 0.19 |

What is claimed is:

1. A method of preparing an anionic initiator by reacting:
   (1) an organolithium compound with (2) a precursor functionalizing agent formed by reacting (a) a diisopropenyl benzene having the formula:

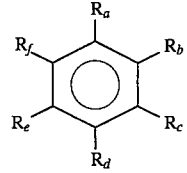

wherein two of the $R_a$–$R_f$ radicals are isopropenyl and the remaining $R_a$–$R_f$ radicals are independently selected from the group consisting of hydrogen, alkyl and cycloalkyl containing 1 to 6 carbon atoms, with (b) a secondary amine having the structural formula:

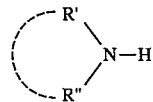

wherein R' and R" are the same or different and are selected from the group consisting of C$_{1-20}$ alkyl groups, C$_{4-20}$ cycloalkyl groups, aryl groups, alkoxy groups, alkoxyalkyl and arylalkyl groups, or R' and R" are linked to form —(CH$_2$)$_p$— wherein p is an integer from 3 to 20, or said secondary amine is a heterocyclic ring compound selected from the group consisting of: piperidine, pyrrolidine, hexamethyleneimine, dodecamethyleneimine, morpholine, thiomorpholine, N-methyl-piperazine, N-aryl-piperazine, 1-(2-pyridyl)-piperazine, pyrrole, 3-pyrroline, pyrazole, imidazole, indole, indoline and purine.

2. The method of claim 1 wherein the organolithium compound comprises the general formula RLi wherein R is selected from the group consisting of alkyl, cycloalkyl, alkenyl, alkynyl, aryl and aralkyl having from 1 to 20 carbon atoms and short chain length low molecular weight polymers from diolefin and vinyl aryl monomers having up to about 25 units.

3. The method of claim 1 wherein the precursor functionalizing agent is formed by reacting a dialkylamine and diisopropenyl benzene.

4. The method of claim 1 wherein the step of forming the precursor functionalizing agent includes the step of reacting the diisopropenyl benzene and the secondary amine in a ratio ranging from at least 1 to 1.

5. The method of claim 1 wherein the step of reacting the organolithium compound and the precursor functionalizing agent includes a step of forming a solution comprising from about 0.2 to 3.0 mmoles of the precursor functionalizing agent per 1 mmole of the organolithium compound in an anhydrous aprotic solvent.

6. A method of preparing an anionic initiator by reacting:
(1) an organolithium compound with (2) a precursor functionalizing agent formed by reacting (a) a diisopropenyl benzene having the formula:

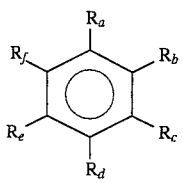

wherein two of the $R_a$–$R_f$ radicals are isopropenyl and the remaining $R_a$–$R_f$ radicals are independently selected from the group consisting of hydrogen, alkyl and cycloalkyl containing 1 to 6 carbon atoms, with (b) a secondary amine is a heterocyclic ring compound selected from the group consisting of: piperidine, pyrrolidine, hexamethyleneimine, dodecamethyleneimine, morpholine, thiomorpholine, N-methyl-piperazine, N-aryl-piperazine, 1-(2-pyridyl)-piperazine, pyrrole, 3-pyrroline, pyrazole, imidazole, indole, indoline and purine and the heterocyclic ring compound is unsubstituted or substituted with one or more substituents selected from the group comprising alkyl, cycloalkyl, aryl, alkoxy, arylalkyl, and alkoxyalkyl groups.

7. A method of preparing an anionic initiator by reacting:
(1) an organolithium compound with (2) a precursor functionalizing agent formed by reacting (a) a diisopropenyl benzene with (b) hexamethyleneimine.

* * * * *